United States Patent

Dehnert et al.

[11] 4,016,152
[45] Apr. 5, 1977

[54] AZO DYE WITH A 2,6-DIAMINO-5-CYANO-OR-5-CARBAMOYL-PYRIDINE COUPLING COMPONENT

[75] Inventors: Johannes Dehnert; Gunther Lamm, both of Ludwigshafen, Germany

[73] Assignee: BASF Aktiengesellschaft, Ludwigshafen (Rhine), Germany

[22] Filed: Aug. 26, 1974

[21] Appl. No.: 500,640

Related U.S. Application Data

[63] Continuation-in-part of Ser. No. 209,431, Dec. 17, 1971, abandoned.

[30] Foreign Application Priority Data

Dec. 19, 1970 Germany .......................... 2062717

[52] U.S. Cl. ..................... 260/156; 260/294.8 R
[51] Int. Cl.² ................. C09B 29/36; D06P 3/24; D06P 3/40; D06P 3/52
[58] Field of Search .................................. 260/156

[56] References Cited

UNITED STATES PATENTS

| | | | |
|---|---|---|---|
| 1,680,108 | 8/1926 | Ostromislensky | 260/156 |
| 1,862,361 | 6/1932 | Dohrn et al. | 260/156 |
| 1,990,923 | 2/1935 | Tisza et al. | 260/156 |
| 2,029,315 | 2/1936 | Engelmann | 260/156 |
| 2,068,353 | 1/1937 | Schneiderwirth | 260/156 |
| 2,148,705 | 2/1939 | Mietzsch et al. | 260/156 X |
| 2,857,372 | 10/1958 | Straley et al. | 260/146 R |
| 3,357,968 | 12/1967 | Wilbert et al. | 260/156 |

FOREIGN PATENTS OR APPLICATIONS 270,987  12/1950  Switzerland ...................... 260/150

*Primary Examiner*—Floyd D. Higel
*Attorney, Agent, or Firm*—Johnston, Keil, Thompson & Shurtleff

[57] ABSTRACT

A dye of the formula

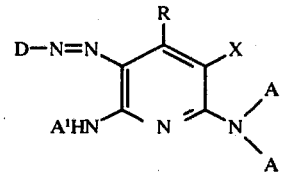

wherein
D is the radical of a diazo component, especially phenyl, phenylazophenyl, benzthiazolyl, benzisothiazolyl, thienyl, thiazolyl, thiadiazolyl and substituted derivatives thereof,
R is hydrogen or alkyl of 1 to 7 carbon atoms,
X is cyano or carbamoyl,
A is a hydrocarbon radical, the two
A's together with the nitrogen form a saturated heterocyclic ring, and
$A^1$ is hydrogen or a hydrocarbon radical.

The dyes are eminently suitable for coloring synthetic fibers, particularly polyesters, brilliant shades.

14 Claims, No Drawings

AZO DYE WITH A 2,6-DIAMINO-5-CYANO-OR-5-CARBAMOYL-PYRIDINE COUPLING COMPONENT

This application is a continuation-in-part of our copending application Ser. No. 209,431, filed Dec. 17, 1971, now abandoned.

The invention relates to dyes of the formula I

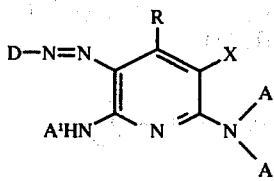 I in which
D is the radical of a diazo component,
R is hydrogen or alkyl of 1 to 7 carbon atoms,
X is cyano or carbamoyl,
A is a hydrocarbon radical, the two
A's together with the nitrogen form a saturated heterocyclic ring, and
$A^1$ is hydrogen or a hydrocarbon radical.

The radical D may be derived for example from an amine of the benzene, benzothiazole, benzoisothiazole, thiazole, thiadiazole, thiophene, azobenzene or anthraquinone series.

The radical D of the diazo component may for example bear the following substituents:

in the benzene series: chloro, bromo. nitro, cyano, trifluoromethyl, methylsulfonyl, ethylsulfonyl, phenylsulfonyl, carbomethoxy, carboethoxy, carbobutoxy, carbo-β-methoxyethoxy, carbo-β-hydroxyethoxy, unsubstituted, N-monosubstituted or N,N-disubstituted carbamoyl or sulfamoyl, methyl, ethyl, methoxy or ethoxy; at least one substituent of the second order (electron-attracting) should be present. Second order substituents are the above substituents other than chloro, bromo, methyl, ethyl, methoxy and ethoxy.

Examples of N-substituents for the carbamoyl and sulfamoyl groups are: methyl, ethyl, propyl, butyl, β-hydroxyethyl, γ-hydroxypropyl, β-methoxyethyl, γ-methoxypropyl, γ-ethoxypropyl, piperidide, pyrrolidide and morpholide.

In the azobenzene series: chloro, bromo, nitro, cyano, ethyl, methyl, ethoxy, methoxy or ethoxy.

In the heterocyclic series; chloro, bromo, nitro, cyano, methyl, ethyl, phenyl, methoxy, ethoxy, methylmercapto, β-carbomethoxyethylmercapto, β-carboethoxyethylmercapto, carbomethoxy, carboethoxy, acetyl, methylsulfonyl or ethylsulfonyl.

The radical D may be specifically derived for example from the following amines:

aniline, o-toluidine, m-toluidine, p-toluidine, o-nitroaniline, m-nitroaniline, p-nitroaniline, o-cyanoaniline, m-cyanoaniline, p-cyanoaniline, 2,4-dicyanoaniline, o-chloroaniline, m-chloroaniline, p-chloroaniline, o-bromoaniline, m-bromoaniline, p-bromoaniline, 2,4,6-tribromoaniline, 2-chloro-4-nitroaniline, 2-bromo-4-nitroaniline, 2-cyano-4-nitroaniline, 2-methylsulfonyl-4-nitroaniline, 2-methyl-4-nitroaniline, 2-methoxy-4-nitroaniline, 4-chloro-2-nitroaniline, 4-methyl-2-nitroaniline, 4-methoxy-2-nitroaniline, 1-amino-2-trifluoromethyl-4-chlorobenzene, 2-chloro-5-aminobenzonitrile, 2-amino-5-chlorobenzonitrile, 1-amino-2-nitrobenzene-4-sulfonic acid n-butylamide or β-methoxyethylamine, 2,4-dinitroaniline, 2,4-dinitro-6-chloroaniline, 2,4-dinitro-6-bromoaniline, 2,4-dinitro-6-cyanoaniline, 1-amino-2,4-dinitrobenzene-6-methylsulfone, 2,6-dichloro-4-nitroaniline, 2,6-dibromo-4-nitroaniline, 2-chloro-6-bromo-4-nitroaniline, 2,6-dicyano-4-nitroaniline, 2-cyano-4-nitro-6-chloroaniline, 2-cyano-4-nitrobromoaniline, 1-aminobenzene-4-methylsulfone, 1-amino-2,6-dibromobenzene-4-methylsulfone, 1-amino-2,6-dichlorobenzene-4-methylsulfone, 1-amino-2,4-dinitrobenzene-6-carboxylic acid methyl or β-methoxyethyl ester, 3,5-dichloroanthranilic acid propyl ester, 3,5-dibromoanthranilic acid β-methoxyethyl ester, N-acetyl-p-phenylenediamine, 4-aminoacetophenone, 4-aminobenzophenone, 2-aminobenzophenone, 2-aminodiphenylsulfone, 4-aminodiphenylsulfone, the methyl, ethyl, propyl, butyl, isobutyl, β-methoxyethyl, β-ethoxyethyl, methyl diglycol, ethyl diglycol, methyl triglycol, ethyl triglycol, β-hydroxyethyl, β-acetoxyethyl, β-(β'-hydroxyethoxy)-ethyl, βhydroxypropyl, γ-hydroxypropyl, ω-hydroxybutyl or ω-hydroxyhexyl ester of 2-aminobenzoic acid, 3-aminobenzoic acid or 4-aminobenzoic acid, the methyl, isobutyl, methyl diglycol, β-methoxyethyl, β-butoxyethyl or β-acetoxyethyl ester of 5-nitroanthranilic acid, the dimethyl, diethyl, dipropyl or dibutyl ester of 3-aminophthalic acid, 4-aminophthalic acid, 5-aminoisophthalic acid or aminoterephthalic acid, the amide, methylamide, propylamide, butylamide, isobutylamide, cyclohexylamide, β-ethylhexylamide, γ-methoxypropylamide, or γ-ethoxypropylamide of 3-aminobenzoic acid or 4-aminobenzoic acid, the dimethylamide, diethylamide, pyrrolidide, morpholide or N-methyl-N-β-hydroxyethylamide of 2-aminobenzoic acid, 3-aminobenzoic acid or 4-aminobenzoic acid, the diamide or bis-γ-methoxypropylamide of 5-aminoisophthalic acid, the bis-diethylamide of aminoterephthalic acid, the imide, γ-hydroxyethylamide or γ-hydroxypropylamide of 3-aminophthalic acid or 4-aminophthalic acid, the β-hydroxyethylamide of 3-amino-6-nitrophthalic acid, the dimethylamide, diethylamide, pyrrolidide or morpholide of 2-aminobenzenesulfonic acid, 3-aminobenzenesulfonic acid or 4-aminobenzenesulfonic acid, the 2'-aminophenyl, 3'-aminophenyl or 4'-aminophenyl ester of methylsulfonic acid, ethylsulfonic acid, butylsulfonic acid or benzenesulfonic acid, 2-aminoanthraquinone, 1-amino-4-chloroanthraquinone, 3-aminodiphenylene oxide, 4-aminodiphenylene oxide, 2-aminobenzothiazole, 2-amino-6-carboxylic acid methyl ester benzothiazole, 2-amino-6-methylsulfonylbenzothiazole, 2-amino-6-cyanobenzothiazole, 2-amino-6-nitrobenzothiazole, 5,6-dichloro-2-aminobenzothiazole, 6,7-dichloro-2-aminobenzothiazole, 4-amino-5-bromo-7-nitro-1,2-benzoisothiazole, 3-amino-5-nitro-2,1-benzoisothiazole, 3-amino-5-nitro-7-bromo-2,1-benzoisothiazole, 2-aminothiazole, 2-amino-5-nitrothiazole, 2-amino-4-methylthiazole-5-carboxylic acid ethyl ester, 2-amino-4-methyl-5-acetylthiazole, 2-amino-3-cyano-4-methylthiophene-5-carboxylic acid esters, 2-phenyl-5-amino-1,3,4-thiadiazole, 3-methylmercapto-5-amino-1,2,4-thiadiazole, 3-β-carbomethoxyethylmercapto-5-amino-1,2,4-thiadiazole, or 2,4-dicyano-3,5-dimethylaniline.

Examples of suitable diazo components of the aminoazobenzene series are: 4-aminoazobenzene, 2',3-dimethyl-4-aminoazobenzene, 3',2-dimethyl-4-aminoazobenzene, 2,5-dimethyl-4-aminoazobenzene, 2-methyl-5-methoxy-4-aminoazobenzene, 2-methyl-4',5-dimethoxy-4-aminoazobenzene, 4'-chloro-2-methyl-5-methoxy-4-aminoazobenzene, 4'-nitro-2-methyl-5-methoxy-4-aminoazobenzene, 4'-chloro-2-methyl-4-aminoazobenzene, 2,5-dimethoxy-4-aminozobenzene, 4'-chloro-2,5-dimethoxy-4-aminoazobenzene, 4'-nitro-2,5-dimethoxy-4-aminoazobenzene, 4'-chloro-2,5-dimethyl-4-aminoazobenzene, 4'-methoxy-2,5-dimethyl-4-aminoazobenzene, 4'-nitro-4-aminoazobenzene, 3,5-dibromo-4-aminoazobenzene, 2,3'-dichloro-4-aminoazobenzene, 3-methoxy-4-aminoazobenzene or 4'-hydroxy-2'-methyl-4-aminoazobenzene.

Examples of radicals R (in addition to hydrogen) are: ethyl, n-propyl, isopropyl, butyl, pentyl, ethylpentyl and preferably methyl.

Radicals $A^1$, apart from hydrogen, are alkyl of one to eight carbon atoms, alkyl substituted by cyano, hydroxy, alkoxy of one to eight carbon atoms, phenoxy, phenoxyethoxy or benzyloxy, cyclohexyl, norbornyl, benzyl, phenylethyl, phenylhydroxyethyl, phenylpropyl, phenylbutyl, phenyl which may be substituted by methoxy, polyalkoxyalkyl, hydroxypolyalkoxyalkyl, alkanoyloxyalkyl or alkoxycarbonylalkyl.

Examples of cyanoalkyl radicals $A^1$ are:
$(CH_2)_2$—CN, $(CH_2)_5$—CN, $(CH_2)_6$—CN, $(CH_2)_7$—CN, $(CH_2)_2$—O—$(CH_2)_2$—CN, $(CH_2)_3$—O—$(CH_2)_2$—CN or $(CH_2)_2$—O—$(CH_2)_2$—O—$(CH_2)_2$—CN.

Examples of specific radicals $A^1$ in addition to those already specified are:

1. unsubstituted or substituted akyl: $CH_3$, $C_2H_5$, n—$C_3H_7$, i—$C_3H_7$, n—$C_4H_9$, i—$C_4H_9$, $C_6H_{13}$,

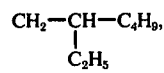

$CH_2CH_2OH$, $(CH_2)_3OH$,

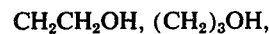

$CH_3$—CH—$CH_2OH$, $(CH_2)_4OH$, $(CH_2)_6OH$,

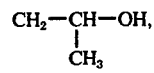

$(CH_2)_2O(CH_2)_2OH$, $(CH_2)_3O(CH_2)_4OH$, $(CH_2)_3OC_2H_4OH$, $(CH_2)_3OC_2H_4OCH_3$, $(CH_2)_3OC_2H_4OC_2H_5$, $(CH_2)_3O(CH_2)_6OH$, $(CH_2)_3OC_2H_4OCH(CH_3)_2$, $(CH_2)_3OC_2H_4OC_4H_9$, $(CH_2)_3OC_2H_4OCH_2C_6H_5$, $(CH_2)_3OC_2H_4OC_2H_4C_6H_5$,

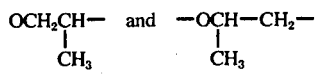

$(CH_2)_3OC_2H_4OC_6H_5$,

the equivalent radicals in which the groupings —$OC_2H_4$—,

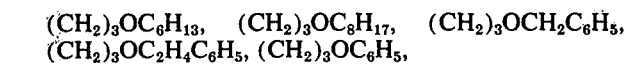

are present twice; $CH_2CH_2OCH_3$, $CH_2CH_2OC_2H_5$, $CH_2CH_2OC_3H_7$, $CH_2CH_2OC_4H_9$, $CH_2CH_2OC_6H_5$, $(CH_2)_3OCH_3$, $(CH_2)_3OC_2H_5$, $(CH_2)_3OC_3H_7$, $(CH_2)_3OC_4H_9$,

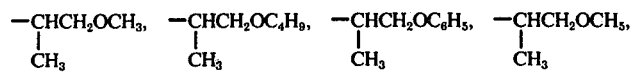

$(CH_2)_3OC_6H_{13}$, $(CH_2)_3OC_8H_{17}$, $(CH_2)_3OCH_2C_6H_5$, $(CH_2)_3OC_2H_4C_6H_5$, $(CH_2)_3OC_6H_5$,

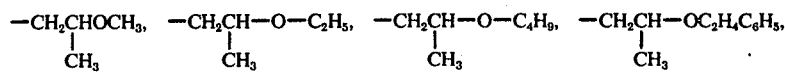

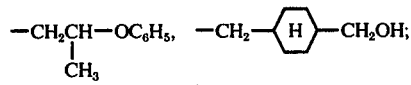

2. unsubstituted or substituted cycloalkyl and polycycloalkyl

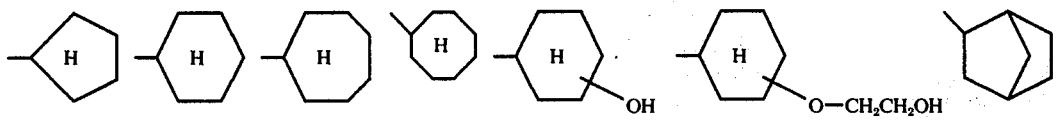

-continued

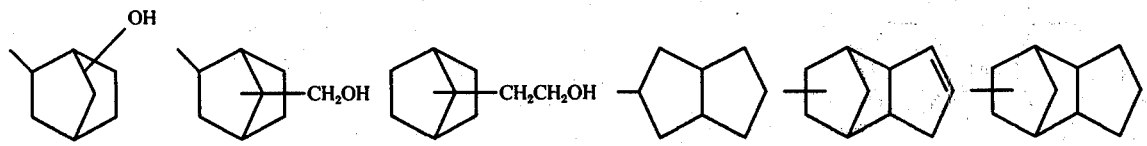

3. aralkyl: $CH_2C_6H_5$, $C_2H_4C_6H_5$,

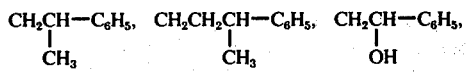

4. phenyl
5. $CH_2CH=CH_2$, $(CH_2)_2COOH$, $(CH_2)_5COOH$ and

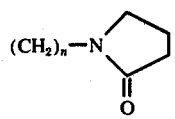

in which $n$ is 2, 3, 4 or 6, $C_2H_4OCOCH_3$, $C_2H_4OCHO$, $C_2H_4OCOCH_3$, $(C_2H_4O)_2COCH_3$, $(C_2H_4O)_2CHO$, $(CH_2)_3OCOCH_3$, $(CH_2)_3OCHO$ and $C_2H_4OCOC_2H_4COOH$.

Examples of preferred substituents $A^1$ are hydrogen, $CH_3$, $C_2H_5$, n-$C_3H_7$, i-$C_3H_7$, n-$C_4H_9$, i-$C_4H_9$, $C_6H_{13}$, $CH_2CH_2OH$, $(CH_2)_3OH$,

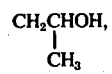

$(CH_2)_4OH$, $(CH_2)_6OH$,

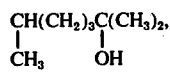

$(CH_2)_2$-O-$(CH_2)_2OH$, $(CH_2)_3O(CH_2)_2OH$, $(CH_2)_3O(CH_2)_4OH$, $(CH_2)_3O(CH_2)_6OH$,

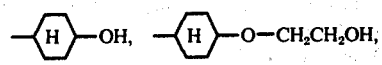

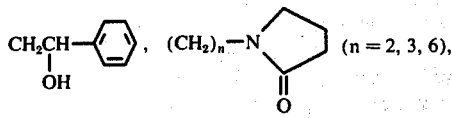

$CH_2CH_2OCH_3$, $CH_2CH_2OC_2H_5$, $CH_2CH_2OC_4H_9$, $(CH_2)_3OCH_3$, $(CH_2)_3OC_2H_5$, $(CH_2)_3OC_3H_7$, $(CH_2)_3OC_4H_9$,

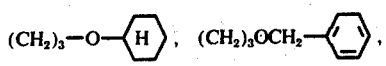

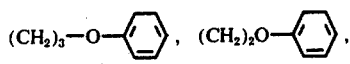

$(CH_2)_3OC_2H_4OCH_3$, $(CH_2)_3OC_2H_4OC_4H_9$, $(CH_2)_3OC_2H_4OC_6H_5$,

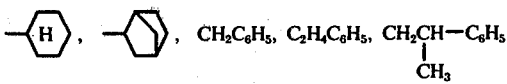

or $C_6H_5$

Radicals A are for example: alkyl of 1 to 4 carbon atoms, hydroxyalkyl of 2 or 3 carbon atoms, alkoxyalkyl of 1 to 4 carbon atoms in the alkoxy and 2 or 3 in the alkyl, cyclohexyl or phenyl.

Specific radicals

are e.g.: $N(CH_3)_2$, $N(C_2H_5)_2$, $N(C_3H_7)_2$, $N(C_4H_9)_2$,

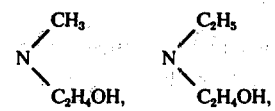

$N(C_2H_4OH)_2$, $N(CH_2CH_2CH_2OH)_2$, $N(CH_2CHOHCH_3)_2$, $N(C_2H_4OCH_3)_2$, $N(C_2H_4OC_2H_5)_2$, $N(C_2H_4OC_4H_9)_2$,

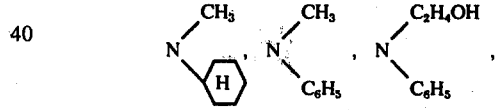

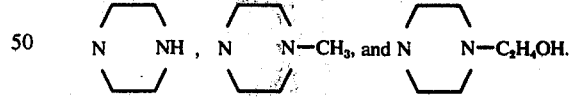

Preferred radicals

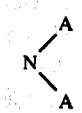

are: $N(CH_3)_2$, $N(C_2H_5)_2$, $N(C_3H_7)_2$, $N(C_4H_9)_2$, $N(C_2H_4OH)_2$,

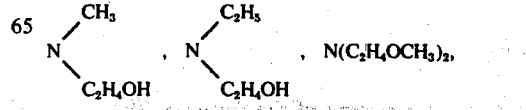

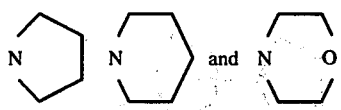

The production of the coupling components is carried out by reacting a compound of the formula

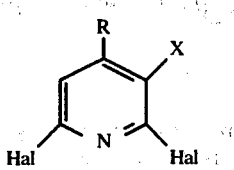

wherein Hal is chloro or bromo, first with the amine of the formula $A^1$-$NH_2$ and then with the secondary amine

When following this sequence, the main product is the isomer of the formula

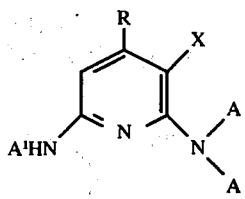

IIIa which is contaminated with the isomer of the formula

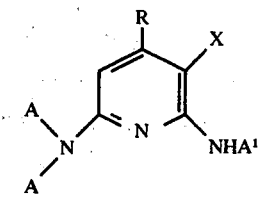

IIIb

Only the isomer IIIa gives valuable dyes. The products obtained by coupling a diazonium salt with the compounds of the formula IIIb are obviously unstable and decompose under dyeing conditions without influencing the quality of the dyeing. It is therefore not necessary to separate the isomers IIIa and IIIb.

Dyes of the formula (I) are prepared by reacting a diazo compound of an amine of the formula (II):

D—$NH_2$  II with a coupling component of the formula (IIIa):

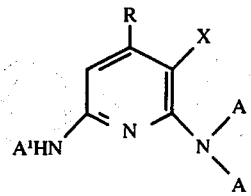

IIIa in which D, R, X, A and $A^1$ have the above meanings.

The amines are diazotized by conventional methods. Coupling is similarly carried out conventionally in aqueous medium with or without adding a solvent, at a strongly to weakly acid reaction.

Specific features of the production of the coupling components and dyes may be taken from the Examples.

In particular, the invention relates to dyes of the formula

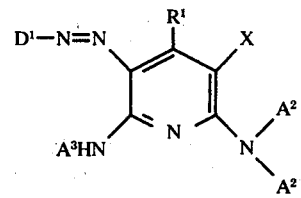

wherein $D^1$ is phenyl substituted by chlorine, bromine, trifluoromethyl, methyl, ethyl, methoxy, nitro, cyano, methylsulfonyl, ethylsulfonyl, phenylsulfonyl, carbalkoxy of a total of 2 to 5 carbon atoms, carbo-$\beta$-alkoxyethoxy, said alkoxy having 1 to 4 carbon atoms, or N,N-dialkylsubstituted sulfamoyl, said alkyl having 1 to 3 carbon atoms; phenylazophenyl; phenylazophenyl substituted by methyl, chlorine, bromine or nitro; benzthiazolyl; benzthiazolyl substituted by nitro, cyano, methylsulfonyl or ethylsulfonyl; benziothiazolyl substituted by chlorine, bromine, cyano or nitro; thiazolyl substituted by cyano or nitro; thienyl substituted by methyl, cyano, nitro or carbalkoxy of a total of 2 to 5 carbon atoms; or thiadiazolyl substituted by phenyl, methyl, chlorine, bromine, methylmercapto, ethylmercapto or alkoxycarbonylethylmercapto; said alkoxy having 1 to 4 carbon atoms;

$R^1$ is hydrogen or alkyl of 1 to 3 carbon atoms;

X is carbamoyl or cyano;

$A^3$ is hydrogen, alkyl of 1 to 8 carbon atoms; alkyl of 2 to 8 carbon atoms substituted by hydroxy, OCHO, $OCOCH_3$, hydroxyalkoxy of 2 to 4 carbon atoms, cyano, alkoxy of 1 to 8 carbon atoms, phenoxy or phenyl; cyclohexyl; norbornyl; phenyl; $\beta$-hydroxy-$\beta$-phenylethyl; or $(CH_2)_3(OC_2H_4)_mOT$ and T is alkyl of 1 to 4 carbon atoms, benzyl or phenyl, m is 1 or 2;

$A^2$ is alkyl of 1 to 4 carbon atoms, hydroxyalkyl of 2 or 3 carbon atoms, alkoxyalkyl of 1 to 4 carbon atoms in the alkoxy and 2 or 3 carbon atoms in the alkyl, cyclohexyl or phenyl and

is pyrrolidino, piperidino, morpholino, hexamethyleneimino, piperazino, N-methylpiperazino or N-β-hydroxyethylpiperazino.

Dyes and dye mixtures of the formula (Ia) are particularly valuable industrially:

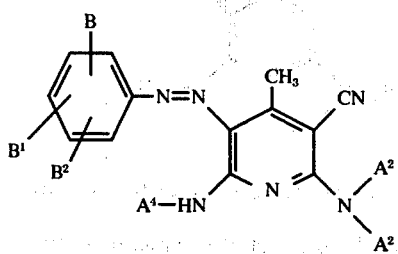

Ia in which

B is nitro, cyano, chloro, bromo, carbomethoxy, carboethoxy, β-methoxycarboethoxy, methylsulfonyl, ethylsulfonyl, methyl, methoxy or phenylazo;

$B^1$ is hydrogen, nitro, chloro, bromo, cyano, methyl, methoxy, carbomethoxy, caroethoxy, methylsulfonyl or ethylsulfonyl; and $B^2$ is hydrogen, chloro, bromo, cyano, methyl, methoxy, carbomethoxy or carboethoxy;

$A^4$ is hydrogen, alkyl of 1 to 8 carbon atoms, hydroxyalkyl of 2 to 8 carbon atoms, alkoxyalkyl of 2 or 3 carbon atoms in the alkyl and 1 to 8 carbon atoms in the alkoxy, $CH_2CH_2OC_2CH_2OH$, $(CH_2)_3OCH_2C-H_2OH$, $(CH_2)_3O(CH_2)_4OH$ or $(CH_2)_3(OC_2H_4)_pOT$, p is 0, 1 or 2, T is alkyl of 1 to 4 carbon atoms, benzyl or phenyl, and

is $N(CH_3)_2$, $N(C_2H_5)_2$, $N(C_3H_7)_2$, $N(C_4H_9)_2$, $N(C_2H_4OH)_2$,

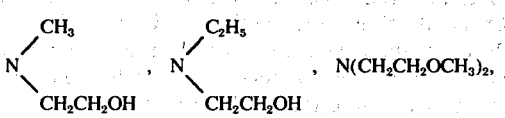

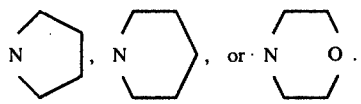

The corresponding dyes which contain as diazo components: benzothiazole, benzoisothiazole, thiazole, thiadiazole or thiophene which may be substituted by nitro, chloro, bromo, cyano, methyl, methylmercapto, β-carbomethoxyethylmercapto, β-carboethoxyethylmercapto, carbomethoxy, carboethoxy or acetyl are also particularly valuable.

The following specific diazo components are particularly valuable: 4-nitroaniline, 2-chloro-4-nitroaniline, 2-bromo-4-nitroaniline, 2-cyano-4-nitroaniline, 2-methoxy-4-nitroaniline, 2-amino-5-nitrophenylsulfonic acid dimethylamide, 2-amino-5-nitrophenylsulfonic acid butylamide, 2-amino-5-nitrophenylsulfonic acid β-methoxyethylamide, 2-aminobenzonitrile, 3-chloro-4-aminobenzonitrile, 2-chloro-5-aminobenzonitrile, 2-amino-5-chloro-benzonitrile, 3,5-dichloro-2-aminobenzonitrile, 1-amino-2,4-dicyanobenzene, 1-amino-2,4-dicyano-6-chlorobenzene, 2-chloro-4-amino-5-nitrbenzonitrile, 2-amino-3-bromo-5-nitrobenzonitrile, 2,6-dicyano-4-nitroaniline, 2,5-dichloro-4-nitroaniline, 2,6-dichloro-4-nitroaniline, 2,6-dibromo-4-nitroaniline, 2-chloro-6-bromo-4-nitroaniline, 2,4-dinitroaniline, 2,4-dinitro-6-chloroaniline, 2,4-dinitro-6-bromoaniline, 2-amino-3,5-dinitrobenzonitrile, 1-amino-4-nitrobenzene-2-methylsulfone, 1-amino-4-nitrobenzene-2-ethylsulfone, 4-methylsulfonyl-aniline, 1-amino-2-chlorobenzene-4-methylsulfone, 1-amino-2,6-dibromobenzene-4-methylsulfone, 1-amino-2,6-dichlorobenzene-4-methylsulfone, esters of 2-aminobenzoic acid, 4-aminobenzoic acid, 2-amino-5-nitrobenzoic acid, 2-amino-3-chloro-5-nitrobenzoic acid, 2-amino-3,5-dichlorobenzoic acid and 2-amino-3,5-dibromobenzoic acid, the methyl or β-methoxyethyl ester of 2-amino-3,5-dinitrobenzoic acid, diethyl 2-aminoterephthalate, 4-aminoazobenzene, 2,3'-dimethyl-4-aminoazobenzene, 2',3-dimethyl-4-aminoazobenzene, 2,5-dimethyl-4-aminoazobenzene, 3,5-dibromo-4-aminoazobenzene and 2,4-dicyano-3,5-dimethylaniline.

Examples of particularly valuable heterocyclic diazo components are as follows: 2-amino-5-nitrothiazole, 2-amino-4-methyl-5-nitrothiazole, 2-amino-4-methylthiazole 5-carboxylic acid ethyl ester, 2-amino-5-phenyl-1,3,4-thiadiazole, 3-phenyl-5-amino-1,2,4-thiadiazole, 3-methylmercapto-5-amino-1,2,4-thiadiazole, 3-β-carbomethoxyethylmercapto-5-amino-1,2,4-thiadiazole, 3-β-carboethoxyethylmercapto-5-amino-1,2,4-thiazole, 2-amino-6-cyanobenzothiazole, 2-amino-6-caboxylic acid methyl ester benzothiazole, 2-amino-6-nitrobenzothiazole, 2-amino-3-cyano-4-methylthiophene-5-carboxylic esters, 3-amino-5-nitro-2,1-benzoisothiazole, 3-amino-5-nitro-7-chloro-2,1-benzoisothiazole, 3-amino-5-nitro-7-bromo-2,1-benzoisothiazole, 4-amino-7-nitro-1,2-benzoisothiazole, 4-amino-5-bromo-1,2-benzoisothiazole, 4-amino-5-bromo-7-nitro-1,2-benzoisthiazole, 4-amino-5-cyano-7-nitro-1,2-benzoisothiazole and 4-amino-5-chloro-7-nitro-1,2-benzoisothiazole.

The new dyes are yellow to blue and are suitable for dyeing textile materials of acrylonitrile polymers, synthetic polyamides, cellulose esters such as secondary cellulose acetate or triacetate, and particularly of synthetic linear polyesters such as polyethylene glycol terephthalate, or polymers having an analogous chemical constitution.

The dyes are also suitable for dyeing in organic solvents such as perchloroethylene and also for the process known as transfer printing provided they sublime at a temperature of from 160° to 240° C. In particular they may be applied however from aqueous dispersion and by the thermosol method. Deep shades are obtained which have excellent fastness properties, particularly fastness to light and heat setting.

The following Examples illustrate the invention. References to parts and percentages are by weight unless otherwise stated.

EXAMPLE 1

187 parts of 2,6-dichloro-3-cyano-4-methylpyridine is stirred at 40° C for 5 hours with 420 parts of a 21% aqueous methylamine solution. The mixture is then diluted with water, filtered, and the residue washed with water and dried, 182 parts of a colorless product (m.p. 136° to 141° C) is obtained which is recrystallized from 3000 parts by volume of benzene. There is obtained about 84 parts of the product of the formula I

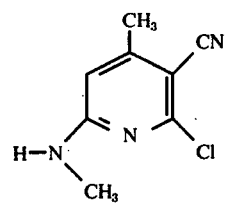

(m.p. 168° to 170° C)
(nmr-spectrum: N—CH₃ 2.87 ppm (CDCl₃))

The product is sparingly soluble in benzene. The residue obtained after removal of the benzene and recrystallization is approx. 84 parts of the product of the formula II

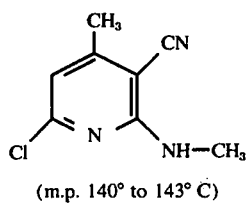

(m.p. 140° to 143° C)

181.5 parts of the product of formula I is stirred with 600 parts by volume of 50% aqueous dimethylamine solution for 6 hours in an autoclave at 140° to 150° C. The mixture is allowed to cool, acidified with concentrated hydrochloric acid and filtered. The filtrate is neutralized to pH 4 to 5, and the precipitate is isolated as usual and dried. 140 parts of the coupling component of the formula III

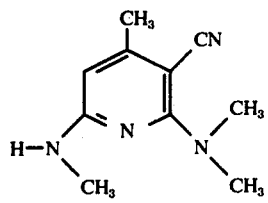

is obtained. It is colorless, melts at 119° and dissolves readily in chloroform.

By treating 2-methylamino-3-cyano-4-methyl-6-chloropyridine (II) with dimethylamine in the same manner, coupling component IV

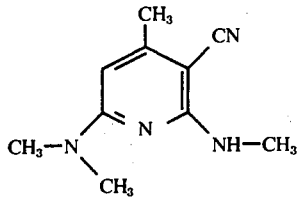

is obtained, which however affords less satisfactory dyes.

7.6 parts of the product of formula III is dissolved in 50 parts by volume of dimethylformamide and the solution combined with a diazo solution, cooled to 0° C, of 7.8 parts of trifluoromethyl-4-chloroaniline, which has been diazotized in sulfuric acid as usual. The pH of the coupling mixture is raised to 2.5 to 3 with sodium acetate at 0° to 5° C.

Upon completion of the coupling, the dye of the formula

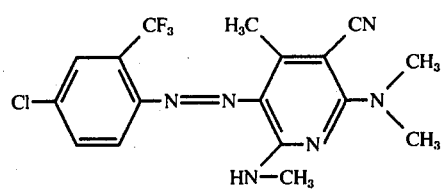

is filtered off, washed with water and dried. Approx. 15 parts of a yellow powder is obtained which colors polyethylene terephthalate fabric yellow shades having good lightfastness. As the dye readily sublimes it is suitable for transfer printing methods.

EXAMPLE 2

187 parts of 2,6-dichloro-3-cyano-4-methylpyridine is stirred at 40' to 45° C for 6 hours with a mixture of 250 parts of 2-hydroxyethylamine and 250 parts by volume of water. Then 2,000 parts by volume of cold water is added and the precipitate filtered off, washed with water and dried. 202 parts of a colorless powder melting at 130° C is obtained. The powder consists of a mixture of the products of the formulae 106 parts of this mixture is stirred in an autoclave for 5 hours at 140° to 150° C with 250 parts of diethylamine. After cooling and isolation, 110 parts of a colorless powder melting at 73° C is obtained. The powder is a mixture of the products of the formulae

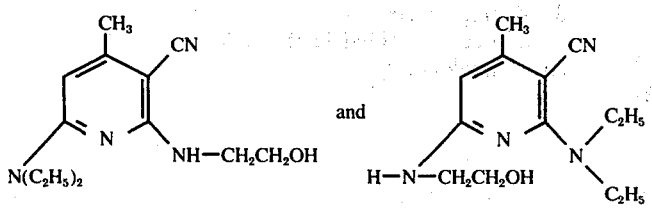

9.9 parts of this mixture is dissolved in 30 parts of dimethylformamide and the mixture added to a diazonium salt solution at 0° C obtained as follows:
9.7 parts of 2-amino-3-bromo-5-nitrobenzonitrile is added at 0° to 5° C to a mixture of 40 parts of 96% sulfuric acid and 13 parts of 44% nitrosylsulfuric acid. The mixture is stirred for 5 hours at 0° to 5° C and then poured onto ice with continued stirring. Then some amidosulfonic acid is added followed by the coupling component(s). Coupling is rapidly completed by raising the pH to 2.5 with 25% caustic soda solution at 0° to 5° C. After filtration, washing and drying, 19.0 parts of a dark red powder is obtained which dissolves in dimethylformamide with a violet color and colors polyethylene terephthalate fabric deep shades having good fastness to light and dry-heat pleating and setting. The coloration is produced by the dye of the formula

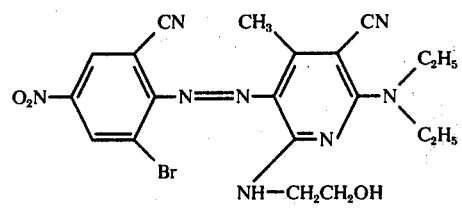

whereas the dye of the formula

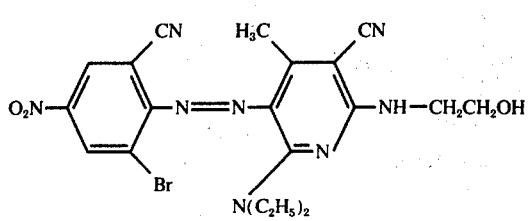

which is also contained in the powder is destroyed in the dyeing process.

EXAMPLE 3

106 parts of the mixture of the compounds of the formulas

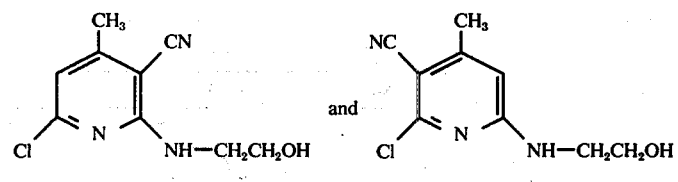

described in Example 2 is stirred with 360 parts by volume of pyrrolidine in an autoclave for 6 hours at 140° to 150° C. After cooling, the resultant colorless product is filtered off, washed with water and dried. 120 parts of a mixture of the compounds of the formulas

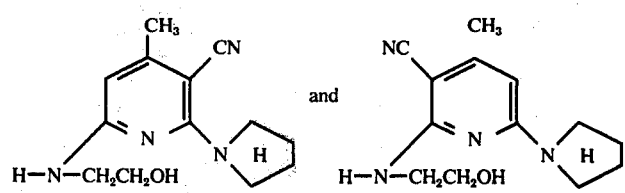

melting at 118° C is obtained.

9.9 parts of this mixture is dissolved in 30 parts by volume of dimethylformamide and the solution added to 9.7 parts of 2-amino-3-bromo-5-nitrobenzonitrile which has been diazotized and poured onto ice in accordance with Example 2. The pH of the mixture is raised to 2.5 with 50% caustic soda solution and the precipitated dye filtered off, washed with water and dried. 19 parts of a reddish brown powder is obtained which dissolved in dimethylformamide with a violet color and colors polyethylene terephthalate material ruby shades having good fastness to light and dry-heat pleating and setting.

The coloration is produced by the dye of the formula

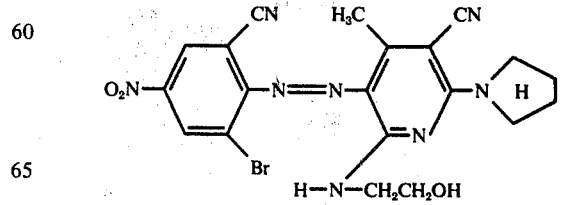

whereas the dye of the formula

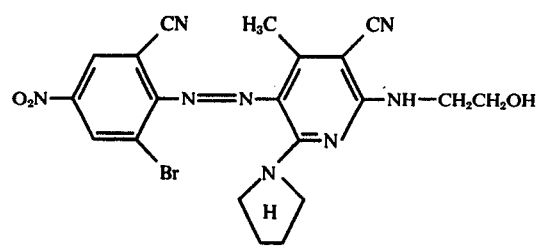

which is also contained in the powder is destroyed in the dyeing process.

The dyes identified in the following Tables are obtained analogously.

TABLE 1

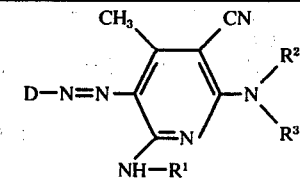

| No. | D | $R^1$ | $R^2$ | $R^3$ | Shade |
|---|---|---|---|---|---|
| 4 | CN, Cl (substituted phenyl) | $C_2H_4OH$ | $C_2H_5$ | $C_2H_5$ | yellow |
| 5 | Cl, Cl, Cl (trichlorophenyl) | " | " | " | " |
| 6 | $O_2N$-, CN (substituted phenyl) | $CH_2CH_2OCH_3$ | $CH_3$ | $CH_2CH_2OH$ | red |
| 7 | " | $CH_2CH_2OH$ | $C_2H_5$ | $C_2H_5$ | red |
| 8 | $O_2N$-, $SO_2CH_3$ | $CH_2CH_2OCH_3$ | $CH_3$ | $CH_2CH_2OH$ | ruby |
| 9 | $O_2N$-benzisothiazole, 3-methyl | " | $C_2H_5$ | " | blue |
| 10 | $O_2N$-, CN | $CH_2CH_2OCH_2CH_2OH$ | " | $C_2H_5$ | red |
| 11 | " | " | $C_3H_7(n)$ | $C_3H_7(n)$ | " |
| 12 | " | $CH_2CH_2OH$ | " | " | " |
| 13 | " | $CH_2CH_2CH_2OH$ | $C_2H_5$ | $C_2H_5$ | " |
| 14 | Cl, $O_2N$- | $CH_2CH_2OH$ | " | " | yellowish red |
| 15 | " | " | $CH_3$ | $CH_3$ | " |
| 16 | " | $CH_2CH_2CH_2OH$ | $C_2H_5$ | $C_2H_5$ | " |
| 17 | " | $CH_2CH_2OCH_2CH_2OH$ | " | " | " |
| 18 | " | $CH_2CH_2CH_2OH$ | $CH_3$ | $CH_3$ | " |
| 19 | $O_2N$-phenyl | " | " | " | orange |
| 20 | " | $CH_2CH_2OH$ | " | " | " |
| 21 | " | " | $C_2H_5$ | $C_2H_5$ | " |
| 22 | " | $CH_2CH_2C_6H_5$ | $CH_2CH_2OH$ | $CH_2CH_2OH$ | " |
| 23 | " | $CH_2CH_2OCH_2CH_2OH$ | $C_2H_5$ | $C_2H_5$ | " |
| 24 | Br, $O_2N$- | $CH_2CH_2OH$ | $CH_3$ | $CH_3$ | yellowish red |

TABLE 1-continued

Structure:
$$D-N=N-\underset{\underset{NH-R^1}{\|}}{\overset{\overset{CH_3}{|}}{C}}\text{-pyridine ring with CN and } N(R^2)(R^3)$$

| No. | D | $R^1$ | $R^2$ | $R^3$ | Shade |
|---|---|---|---|---|---|
| 25 | " | " | $C_2H_5$ | $C_2H_5$ | " |
| 26 | " | $CH_2CH_2CH_2OH$ | " | " | " |
| 27 | " | $CH_2CH(CH_3)OH$ | " | " | " |
| 28 | 2-CN-phenyl | " | $C_2H_4OCH_3$ | $C_2H_4OCH_3$ | yellow |
| 29 | " | $CH_2CH_2OH$ | " | " | " |
| 30 | 2-CF$_3$-phenyl | " | " | " | " |
| 31 | " | $CH_2CH_2-C_6H_5$ | $CH_2CH_2OH$ | $CH_3$ | " |
| 32 | " | " | " | $CH_2CH_2OH$ | " |
| 33 | " | $CH_2CH(CH_3)-C_6H_5$ | " | " | yellow (polyamide) |
| 34 | " | $CH_2CH_2N$(pyrrolidinone) | " | $CH_3$ | " |
| 35 | 4-Cl-2-CF$_3$-phenyl | " | " | " | " |
| 36 | " | $CH_2CH_2CH_2OC_6H_5$ | $CH_2CH_2OH$ | $CH_2CH_2OH$ | " |
| 37 | " | $(CH_2)_6OH$ | $CH_2CH_2OCH_3$ | $CH_2CH_2OCH_3$ | " |
| 38 | 3,5-Cl$_2$-4-NO$_2$-phenyl | $CH_2CH_2OH$ | $C_2H_5$ | $C_2H_5$ | red |
| 39 | " | $CH_2CH_2CH_2OH$ | " | " | " |
| 40 | " | $CH_2CH_2OCH_2CH_2OH$ | " | " | " |
| 41 | 3,5-Br$_2$-4-NO$_2$-phenyl | " | " | " | " |
| 42 | " | $CH_2CH_2OH$ | " | " | " |
| 43 | 2,4-(NO$_2$)$_2$-phenyl | " | " | " | bluish red |
| 44 | " | $CH_2CH_2CH_2OH$ | " | " | " |
| 45 | " | $CH_2CH_2OCH_2CH_2OH$ | " | " | " |
| 46 | 2-CN-4-NO$_2$-6-Cl-phenyl | " | " | " | ruby |
| 47 | " | " | $CH_3$ | $CH_3$ | " |

TABLE 1-continued

Structure: D—N=N— attached to a pyridine ring with CH₃, CN, NR²R³, and NH—R¹ substituents.

| No. | D | R¹ | R² | R³ | Shade |
|---|---|---|---|---|---|
| 48 | 2-CN, 4-NO₂, 6-Cl, 3-CH₃ phenyl | CH₂CH₂OCH₂CH₂OH | C₃H₇(n) | C₃H₇(n) | " |
| 49 | 2-SO₂CH₃, 4-NO₂, 5-CH₃ phenyl | " | " | " | bluish red |
| 50 | " | " | " | " | " |
| 51 | phenyl-N=N-(p-tolyl) | " | C₂H₅ | C₂H₅ | orange |
| 52 | " | CH₂CH₂OH | CH₃ | CH₂CH₂OH | " |
| 53 | " | CH₂CH₂CH₂OH | " | " | " |
| 54 | (4-Cl-phenyl)-N=N-(p-tolyl) | " | " | " | " |
| 55 | 3-CH₃, 4-CN, 5-CO₂CH₃ thiophene | " | C₂H₅ | C₂H₅ | bluish red |
| 56 | " | CH₂CH₂OH | " | " | " |
| 57 | " | " | CH₃ | CH₃ | " |
| 58 | " | CH₂CH₂OCH₂CH₂OH | C₂H₅ | C₂H₅ | " |
| 59 | 2-NO₂, 5-CH₃ thiazolyl | " | " | " | violet |
| 60 | 5-NO₂, 3-CH₃ benzisothiazolyl | " | " | " | navy |
| 61 | " | CH₂CH₂CH₂OH | " | " | " |
| 62 | " | CH₂CH₂OH | " | " | " |
| 63 | " | " | " | " | " |
| 64 | " | " | CH₃ | CH₃ | " |
| 65 | " | CH₂CH₂CH₂OH | " | " | " |
| 66 | 5-NO₂, 7-Cl, 3-CH₃ benzisothiazolyl | " | C₂H₅ | C₂H₅ | blue |
| 67 | " | CH₂CH₂OH | " | " | " |
| 68 | 3-SCH₃ thiadiazolyl | " | " | " | orange |
| 69 | " | CH₂CH₂CH₂OH | " | " | " |
| 70 | 3-(S-C₂H₄-OC(O)CH₃) thiadiazolyl | CH₂CH₂OH | C₂H₅ | C₂H₅ | " |

TABLE 1-continued

[Structure: D—N=N— pyridine with CH₃, CN, NR²R³, NH—R¹ substituents]

| No. | D | R¹ | R² | R³ | Shade |
|-----|---|-----|-----|-----|-------|
| 71 | " | " | C₂H₄OCH₃ | C₂H₄OCH₃ | " |
| 72 | 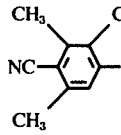 (CH₃, CN, NC, CH₃ benzene) | CH₂CH₂OH | C₂H₅ | C₂H₅ | yellowish red |
| 73 | " | CH₂CH₂OCH₂CH₂OH | " | " | " |
| 74 | 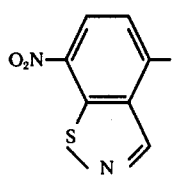 (O₂N, benzisothiazole with CH₃) | " | " | " | bluish red |
| 75 | " | CH₂CH₂OH | " | " | " |
| 76 | 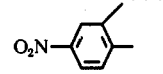 (O₂N, COOCH₃ benzene) | " | " | " | red |
| 77 | " | CH₂CH₂CH₂OH | " | " | " |
| 78 | " | CH₂CH₂OH | C₄H₉(n) | C₄H₉(n) | " |
| 79 | 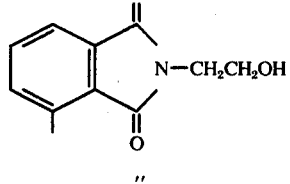 (phthalimide N—CH₂CH₂OH with CH₃) | " | C₂H₅ | C₂H₅ | yellow |
| 80 | " | " | C₂H₄OCH₃ | C₂H₄OCH₃ | yellow (polyamide) |
| 81 | " | " | C₂H₄OH | C₂H₄OH | " |
| 82 | 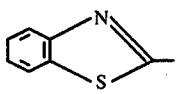 (benzothiazole) | " | C₂H₅ | C₂H₅ | yellowish red |
| 83 | 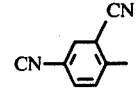 (O₂N-benzothiazole) | " | " | " | " |
| 84 | " | CH₂CH₂OCH₂CH₂OH | " | " | " |
| 85 | 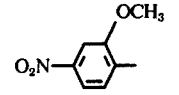 (CN, CN, CH₃ benzene) | " | " | " | " |
| 86 | " | CH₂CH₂CH₂OH | " | " | " |
| 87 | 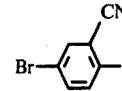 (OCH₃, O₂N benzene) | " | " | " | red |
| 88 | " | CH₂CH₂OH | " | " | " |
| 89 | " | CH₂CH₂OCH₂CH₂OH | " | " | " |
| 90 | (Br, CN benzene) | " | " | " | yellow |
| 91 | " | CH₂CH—C₆H₅ \| OH | CH₃ | CH₂CH₂OH | yellow (polyamide) |

TABLE 1-continued

Structure:
D—N=N— [pyridine ring with CH₃, CN, NR²R³, NH—R¹ substituents]

| No. | D | R¹ | R² | R³ | Shade |
|---|---|---|---|---|---|
| 92 | " | cyclohexyl | CH₂CH₂OH | CH₂CH₂OH | " |
| 93 | 2-methyl-3,5-dinitro-6-chlorophenyl (NO₂, O₂N, Cl substituents) | CH₂CH₂OH | C₂H₅ | C₂H₅ | bluish red |
| 94 | " | CH₂CH₂CH₂OH | " | " | " |
| 95 | 5-chloro-2-methyl-SO₂CH₃-phenyl | " | " | " | yellow (polyamide) |
| 96 | 2-methyl-3,5-dinitro-6-cyanophenyl | " | " | " | violet |
| 97 | " | CH₂CH₂OH | " | " | " |
| 98 | " | " | C₃H₇(n) | C₃H₇(n) | " |
| 99 | 2,4-dichloro-6-methylphenyl | " | C₂H₅ | C₂H₅ | yellow |

TABLE 2

Structure:
D—N=N— [pyridine ring with R², CN, X, H—N—R¹ substituents]

| No. | D | X | R¹ | R² | Shade |
|---|---|---|---|---|---|
| 100 | 2-methylbenzonitrile | piperidino (N—H) | CH₂CH₂OCH₂CH₂OH | CH₃ | yellow |
| 101 | " | " | " | C₃H₇(n) | " |
| 102 | " | piperidino (N—H) | " | " | " |
| 103 | 4-nitrophenyl-methyl | " | " | CH₃ | orange |
| 104 | " | piperidino (N—H) | " | " | " |
| 105 | " | " | CH₂CH₂OH | " | " |

TABLE 2-continued

[Structure: D—N=N— attached to pyridine ring with R², CN, X, N, and H—N—R¹ substituents]

| No. | D | X | R¹ | R² | Shade |
|---|---|---|---|---|---|
| 106 | O₂N—C₆H₃(CH₃)— | " | " | " | " |
| 107 | " | " | CH₂CH₂OCH₂CH₂OH | " | " |
| 108 | " | " | " | C₂H₅ | " |
| 109 | " | " | " | C₃H₇(n) | " |
| 110 | O₂N—C₆H₃(OCH₃)— | " | " | C₂H₅ | red |
| 111 | " | " | CH₂CH₂CH₂OH | CH₃ | " |
| 112 | O₂N—C₆H₃(Cl)— | " | " | " | " |
| 113 | " | " | CH₂CH₂OH | " | " |
| 114 | " | " | CH₂CH₂OCH₂CH₂OH | " | " |
| 115 | " | N(C₂H₅)₂ | (CH₂)₃OCH₂CH₂OC₆H₅ | " | red |
| 116 | O₂N—C₆H₃(CN)— | " | " | " | " |
| 117 | O₂N—C₆H₂(CN)(Cl)— | piperidino | CH₂CH₂OH | " | ruby |
| 118 | " | " | CH₂CH₂CH₂OH | " | reddish violet |
| 119 | " | " | CH₂CH₂OCH₂CH₂OH | " | ruby |
| 120 | O₂N—C₆H₂(CN)(Br)— | " | CH₂CH₂CH₂OH | " | reddish violet |
| 121 | " | " | CH₂CH₂OCH₂CH₂OH | " | ruby |
| 122 | " | " | " | C₂H₅ | " |
| 123 | " | piperidino | " | CH₃ | " |
| 124 | O₂N—C₆H₂(CN)(Cl)— | " | " | " | " |
| 125 | O₂N—C₆H₂(CN)(NO₂)— | " | " | " | violet |

TABLE 2-continued

Structure: D—N=N—C(R²)=C(CN)—C(X)=N—C(=N—H...R¹ H-N-R¹)

| No. | D | X | R¹ | R² | Shade |
|---|---|---|---|---|---|
| 126 | '' | piperidine (NH) | '' | '' | '' |
| 127 | '' | '' | CH₂CH₂CH₂OH | '' | '' |
| 128 | 2,4-dinitro-6-chloro-phenyl (NO₂, O₂N, Cl) | '' | '' | '' | '' |
| 129 | 2,4-dinitrophenyl (NO₂, O₂N) | '' | '' | '' | reddish violet |
| 130 | '' | '' | CH₂CH₂OH | '' | '' |
| 131 | '' | '' | CH₂CH₂OCH₂CH₂OH | '' | '' |
| 132 | '' | piperidine (NH) | '' | '' | ruby |
| 133 | 3,5-dichloro-4-nitro-phenyl (Cl, O₂N, Cl) | '' | '' | '' | red |
| 134 | '' | piperidine (NH) | '' | '' | '' |
| 135 | 2-bromo-4-nitro-6-chloro-phenyl (Br, O₂N, Cl) | '' | '' | '' | '' |
| 136 | '' | homopiperazine (N, NH) | '' | '' | '' |
| 137 | 2,6-dichloro-4-nitro-phenyl (Cl, O₂N, Cl) | '' | '' | '' | '' |
| 138 | 2,4-dichlorophenyl (Cl, Cl) | piperidine (NH) | CH₂CH₂OH | '' | yellow |
| 139 | '' | '' | CH₂CH₂CH₂OH | '' | '' |
| 140 | '' | '' | CH₂CH₂OCH₂CH₂OH | '' | '' |

TABLE 2-continued

[Structure: D—N=N— attached to a ring with R² and CN on one carbon, X on another, and =N—NH—R¹]

| No. | D | X | R¹ | R² | Shade |
|---|---|---|---|---|---|
| 141 | " | piperidine (N,H) | " | " | " |
| 142 | " | piperazine (N,NH) | CH₂CH₂OH | " | " |
| 143 | " | N-methylpiperazine (N,NCH₃) | " | " | " |
| 144 | " | " | CH₂CH₂OCH₂CH₂OH | " | " |
| 145 | 2-cyanophenyl (CN) | " | " | " | " |
| 146 | " | morpholine (N,O) | " | " | " |
| 147 | " | " | CH₂CH₂OH | " | " |
| 148 | " | " | " | C₃H₇(n) | " |
| 149 | 2-nitro-5-thiazolyl (O₂N—thiazole) | piperidine (N,H) | " | CH₃ | violet |
| 150 | " | " | CH₂CH₂CH₂OH | " | " |
| 151 | " | " | CH₂CH₂OCH₂CH₂OH | " | " |
| 152 | " | piperidine (N,H) | " | " | reddish violet |
| 153 | methyl 3-methyl-4-cyano-5-thiophene carboxylate | " | " | " | red |
| 154 | 7-nitro-4-methyl-benzisothiazolyl | N(C₂H₅)₂ | " | " | ruby |
| 155 | " | piperidine (N,H) | " | " | reddish violet |

TABLE 2-continued
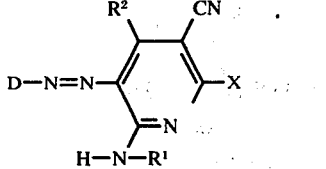
| No. | D | X | R¹ | R² | Shade |
|---|---|---|---|---|---|
| 156 | 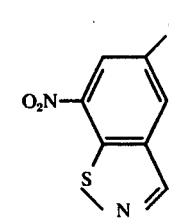 | " | " | " | violet |
| 157 |  | 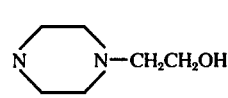 | $CH_2CH_2OH$ | " | yellow (polyamide) |
| 158 | " |  | " | " | yellow |
| 159 | " | 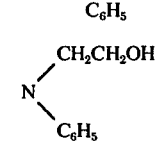 | " | " | " |
| 160 | 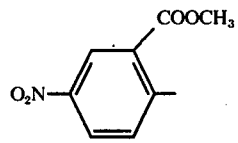 | 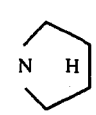 | $CH_2CH_2OH$ | " | red |
| 161 | " | " | $CH_2CH_2CH_2OH$ | " | " |
| 162 | 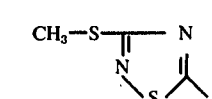 | " | " | " | orange |
| 163 | 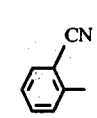 |  | $(CH_2)_5CN$ | " | yellow |
| 164 | 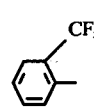 | " | " | " | " |
| 165 | " | " | $CH_2CH_2OCH_2CH_2OCHO$ | " | " |
| 166 | 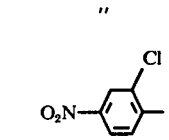 | N (CH₂)₆ | $CH_2CH_2OCH_2CH_2OH$ | " | yellowish red |

TABLE 3

Structure: pyridine ring with CH₃ and X substituents, D—N=N— group, A substituent, and H—N—R¹ group.

| No. | D | R¹ | A | X | Shade |
|-----|---|----|----|----|-------|
| 167 | 2-cyanophenyl | CH₂CH₂OH | N(CH₂CH₂OH)₂ | CN | yellow (polyamide) |
| 168 | 4-(phenylazo)phenyl | " | N(C₂H₅)₂ | CONH₂ | red |
| 169 | " | " | piperidino (N H) | " | " |
| 170 | " | CH₂CH₂OCH₂CH₂OH | " | " | " |
| 171 | 4-(phenylazo)-3-methylphenyl | " | " | " | " |
| 172 | 4-chloro-2-(trifluoromethyl)phenyl | CH₂CH₂OH | " | " | yellow |
| 173 | 2-cyano-3-nitro-... (O₂N, CN substituted phenyl) | CH₂CH₂OH | morpholino (N O) | CN | ruby |
| 174 | 2-cyano-...-Br phenyl | CH₂—CH=CH₂ | N(CH₂CH₂OCH₃)₂ | " | yellow |
| 175 | O₂N, CN, Cl substituted phenyl | CH₂CH₂CH₂OCH₃ | piperidino (N H) | " | reddish violet |
| 176 | " | CH₂CH₂OCH₂CH₂OH | " | CONH₂ | violet |
| 177 | O₂N, CN, Br substituted phenyl | " | " | " | " |

We claim:
1. A dye of the formula

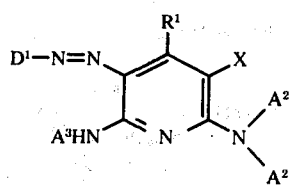

where
D¹ is phenyl substituted by chlorine, bromine, trifluoromethyl, methyl, ethyl, methoxy, nitro, cyano, methylsulfonyl, ethylsulfonyl, phenylsulfonyl, carbalkoxy of a total of 2 to 5 carbon atoms, carbo-β-alkoxyethoxy, said alkoxy having 1 to 4 carbon atoms or N,N-dialkyl-substituted sulfamoyl, said alkyl having 1 to 3 carbon atoms; phenylazophenyl; phenylazophenyl substituted by methyl, chlorine, bromine or nitro; benzthiazolyl; benzthiazolyl substituted by nitro, cyano, methylsulfonyl or ethylsulfonyl; benzisothiazolyl substituted by chlorine, bromine, cyano or nitro; thiazolyl substituted by cyano or nitro; thienyl substituted by methyl, cyano, nitro or carbalkoxy of a total of 2 to 5 carbon atoms; or thiadiazolyl substituted by phenyl, methyl, chlorine, bromine, methylmercapto, ethylmercapto or alkoxycarbonylethylmercapto, said alkoxy having 1 to 4 carbon atoms;

R[1] is hydrogen or alkyl of 1 to 3 carbon atoms;

X is carbamoyl or cyano;

A[3] is hydrogen, alkyl of 1 to 8 carbon atoms; alkyl of 2 to 8 carbon atoms substituted by hydroxy, OCHO, OCOCH$_3$, hydroxyalkoxy of 2 to 4 carbon atoms, cyano, alkoxy of 1 to 8 carbon atoms, phenoxy or phenyl; cyclohexyl; norbornyl; phenyl; β-hydroxy-β-phenylethyl; or (CH$_2$)$_3$(OC$_2$H$_4$)$_m$OT and T is alkyl of 1 to 4 carbon atoms, benzyl or phenyl, m is 1 to 2, each A[2], which can be the same or different, is alkyl of 1 to 4 carbon atoms, hydroxyalkyl of 2 or 3 carbon atoms, alkoxyalkyl of 1 to 4 carbon atoms in the alkoxy and 2 or 3 carbon atoms in the alkyl, cyclohexyl or phenyl and

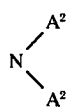

is pyrrolidino, piperidino, morpholino, hexamethyleneimino, piperazino, N-methylpiperazino or N-β-hydroxyethylpiperazino.

2. A dye according to the formula in claim 1, wherein D[1] is

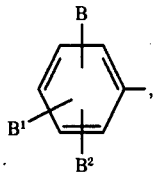

B is nitro, cyano, chloro, bromo, trifluoromethyl, carbomethoxy, carboethoxy, carbo-β-methoxyethoxy, methylsulfonyl, ethylsulfonyl or phenylazo, B[1] is hydrogen, nitro, chloro, bromo, cyano, methyl, methoxy carbomethoxy or carboethoxy and B[2] is hydrogen, chloro or cyano.

3. A dye according to the formula in claim 1, where X is cyano.

4. A dye as claimed in claim 1 of the formula

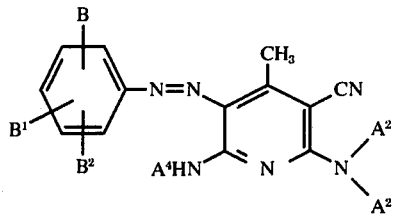

wherein

B is nitro, cyano, chloro, bromo, carbomethoxy, carboethoxy, β-methoxycarboethoxy, methylsulfonyl, ethylsulfonyl, methyl, methoxy or phenylazo;

B[1] is hydrogen, nitro, chloro, bromo, cyano, methyl, methoxy, carbomethoxy, carboethoxy, methylsulfonyl or ethylsulfonyl; and B[2] is hydrogen, chloro, bromo, cyano, methyl, methoxy, carbomethoxy or carboethoxy;

A[4] is hydrogen, alkyl of 1 to 8 carbon atoms, hydroxyalkyl of 2 to 8 carbon atoms, alkoxyalkyl of 2 or 3 carbon atoms in the alkyl and 1 to 8 carbon atoms in the alkoxy, CH$_2$CH$_2$OCH$_2$CH$_2$OH, (CH$_2$)$_3$OCH$_2$CH$_2$OH, (CH$_2$)$_3$O(CH$_2$)$_4$OH or (CH$_2$)$_3$(OC$_2$H$_4$)$_p$OT, p is 1 or 2, T is alkyl of 1 to 4 carbon atoms, benzyl or phenyl, and

is N(CH$_3$)$_2$, N(C$_2$H$_5$)$_2$, N(C$_3$H$_7$)$_2$, N(C$_4$H$_9$)$_2$, N(C$_2$H$_4$OH)$_2$,

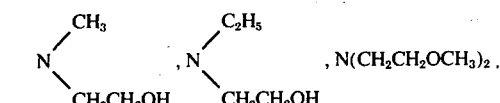

5. A dye according to the formula in claim 1 where A[3] is alkyl of 1 to 6 carbon atoms, hydroxyalkyl of 2 to 6 carbon atoms, alkoxyethyl of a total of 3 to 5 carbon atoms, alkoxypropyl of a total of 4 to 6 carbon atoms, phenylalkyl of a total of 7 to 10 carbon atoms, cyclohexyl, norbornyl, β-hydroxy-β-phenylethyl, phenoxyethyl, phenoxypropyl, benzyloxypropyl, γ-phenoxyethoxypropyl, CH$_2$CH$_2$OCH$_2$CH$_2$OH, (CH$_2$)$_3$OCH$_2$CH$_2$OH, (CH$_2$)$_3$O(CH$_2$)$_4$OH or (CH$_2$)$_3$(OC$_2$H$_4$)$_m$OT[1], T[1] is alkyl of 1 to 4 carbon atoms and m is 1 or 2.

6. A dye according to the formula in claim 1 where

is N-(CH$_3$)$_2$, N(C$_2$H$_5$)$_2$, N(C$_3$H$_7$)$_2$, N(C$_4$H$_9$)$_2$, N(C$_2$H$_4$OH)$_2$,

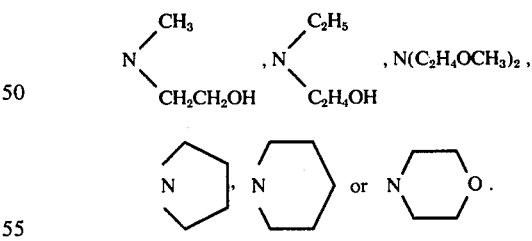

7. A dye of the formula

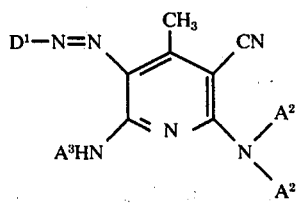

in which $D^1$ has the meanings given in claim 2,
$A^3$ has the meanings given in claim 5 and
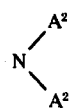
has the meanings given in claim 6.
8. The dye of the formula
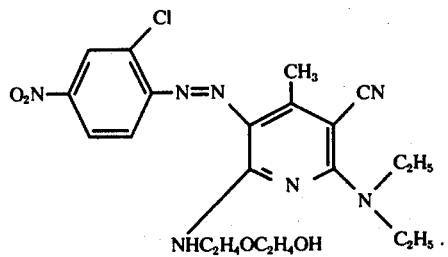
9. The dye of the formula
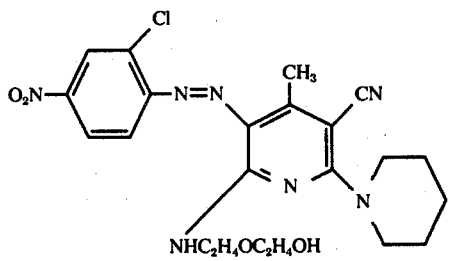
10. The dye of the formula
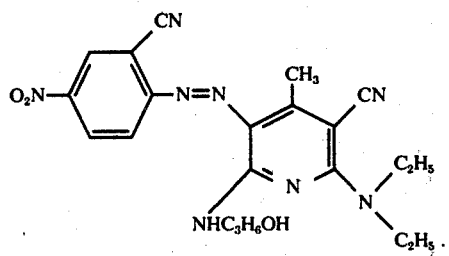
11. The dye of the formula
12. The dye of the formula
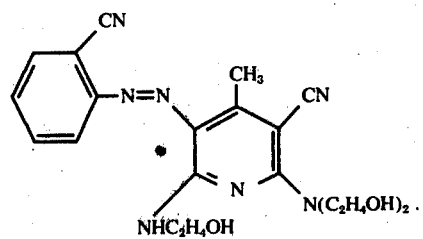
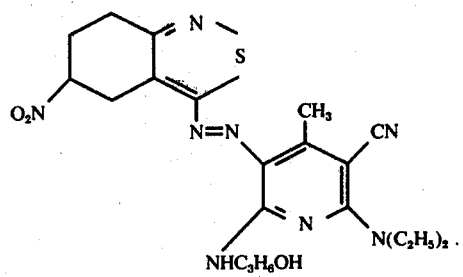
13. The dye of the formula
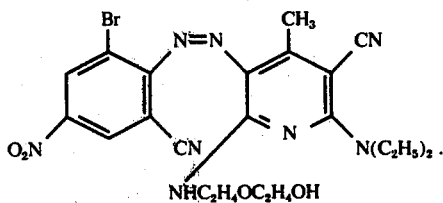
14. The dye of the formula
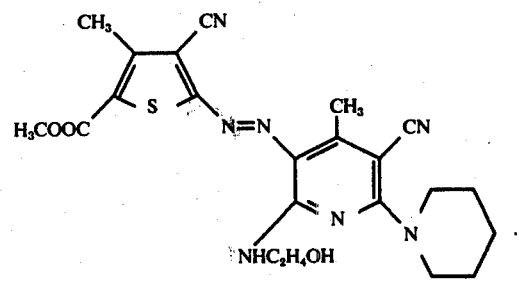
* * * * *